Figure 1A:
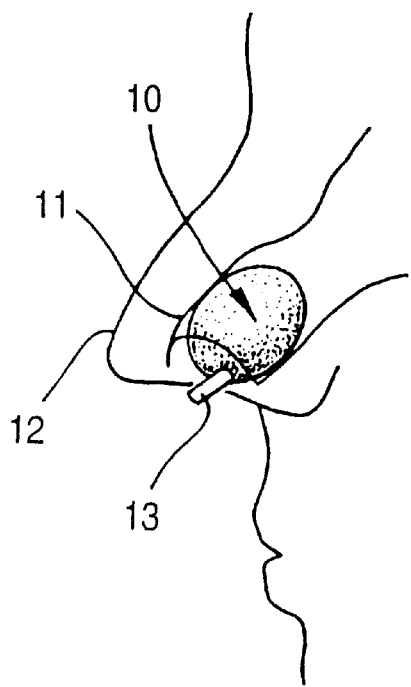
Figure 1B:
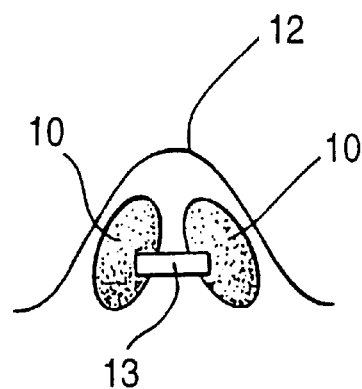
Figure 1C:
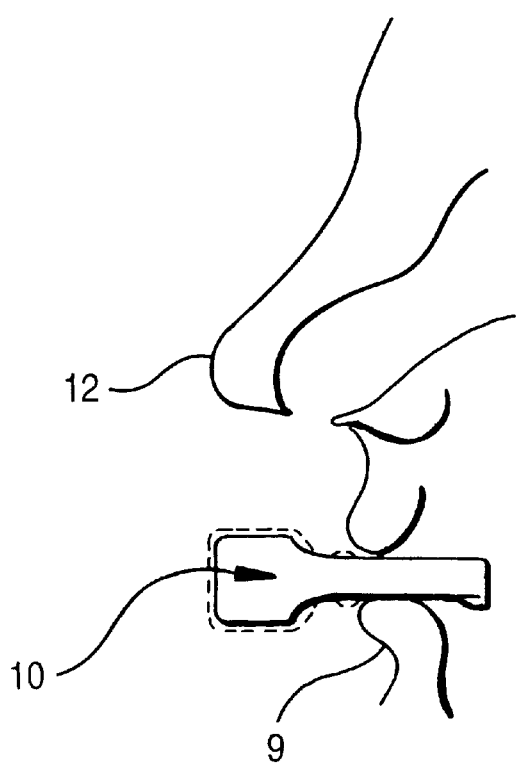
Figure 2A:
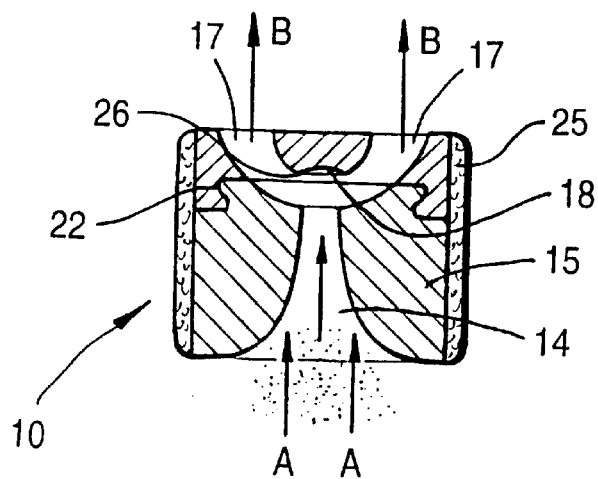
Figure 2B:
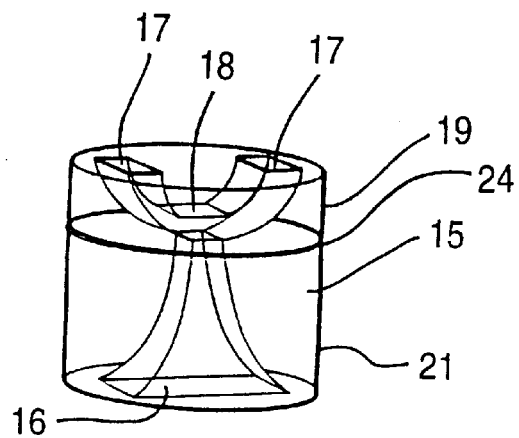

United States Patent
Tovey

[19]

[11] Patent Number: 6,109,262
[45] Date of Patent: *Aug. 29, 2000

[54] NASAL AND ORAL FILTERS

[75] Inventor: Euan R. Tovey, Petersham, Australia

[73] Assignee: University of Sydney, Sydney, Australia

[*] Notice: This patent is subject to a terminal disclaimer.

[21] Appl. No.: 09/121,820

[22] Filed: Jul. 24, 1998

Related U.S. Application Data

[63] Continuation of application No. 08/793,487, filed as application No. PCT/AU95/00540, Aug. 25, 1995, Pat. No. 5,787,884.

[30] Foreign Application Priority Data

Aug. 26, 1994 [AT] Austria .......................................... 7659

[51] Int. Cl.⁷ .................................................. A61G 10/00
[52] U.S. Cl. ............................. 128/206.11; 128/204.12; 128/204.13
[58] Field of Search .......................... 128/206.11, 204.12, 128/204.13, 205.29

[56] References Cited

U.S. PATENT DOCUMENTS

| | | | |
|---|---|---|---|
| 682,478 | 9/1901 | Martin | 128/205.29 |
| 2,526,586 | 10/1950 | Shuff | 128/206.11 |
| 3,457,927 | 7/1969 | Siagusa | 128/205.29 |
| 4,220,150 | 9/1980 | King . | |
| 4,221,217 | 9/1980 | Amezcua | 128/206.11 |
| 4,401,117 | 8/1983 | Gershuny . | |
| 4,827,923 | 5/1989 | Bishop et al. . | |
| 5,117,820 | 6/1992 | Robitaille | 128/206.11 |
| 5,787,884 | 8/1998 | Tovey | 128/206.11 |

FOREIGN PATENT DOCUMENTS

| | | | |
|---|---|---|---|
| 2 536 659 | of 0000 | France . | |
| 2 417 304 | of 1979 | France . | |
| 2504003 | 10/1982 | France | 128/206.11 |
| 2 594 033 | 8/1987 | France . | |
| 135661 | 12/1929 | Switzerland | 128/206.11 |
| 386618 | 2/1964 | Switzerland | 128/205.29 |
| 28819 | 2/1905 | United Kingdom | 128/206.11 |
| 262300 | 12/1926 | United Kingdom | 128/206.11 |
| 315091 | 7/1929 | United Kingdom | 128/206.11 |
| 1231800 | 5/1971 | United Kingdom . | |
| 2 216 806 | 10/1989 | United Kingdom . | |

*Primary Examiner*—John G. Weiss
*Assistant Examiner*—Charles W. Anderson
*Attorney, Agent, or Firm*—Nixon & Vanderhye

[57] ABSTRACT

Particle entrapment device for the capture of particles in an inhaled, or an exhaled air stream, including a body having a portion adapted to fit within the mouth or at least one nostril of a human, or other mammalian animal, in sealing engagement with the edges of that orifice, and a passage through the body to allow air to be inhaled by, or to be exhaled by the animal through the particle entrapment device. The passage has a non-linear path and includes a collector means so placed in the passage that, during inhalation, air is drawn firstly towards and then secondly around the collector to that particulate matter in the air inhaled by the animal will be caused to impact against the collector due to the non-linearity of the passage and to be retained on the collector such that the particulate matter retained on the collector is prevented from entering the airways of the animal. The collector is removable from the particle entrapment device to allow analysis of the particles impacted thereon.

4 Claims, 3 Drawing Sheets

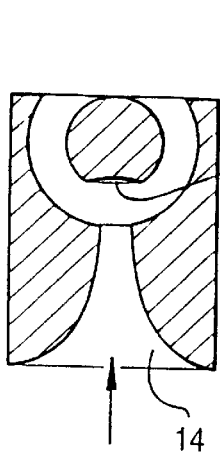
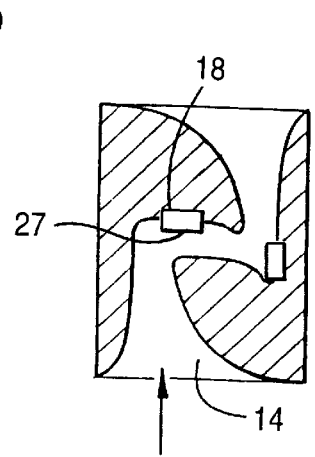
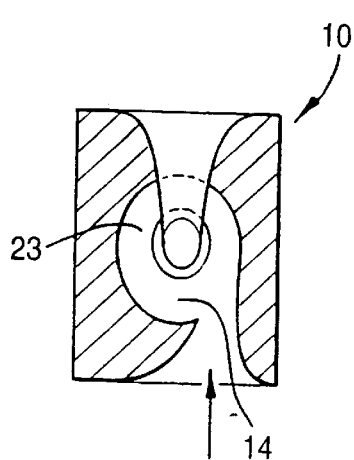
FIG. 3a          FIG. 3b          FIG. 3c
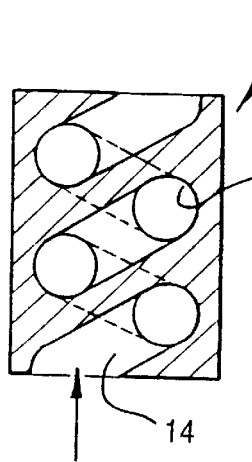
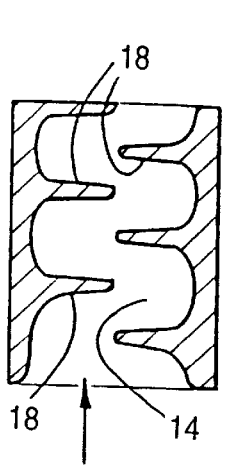
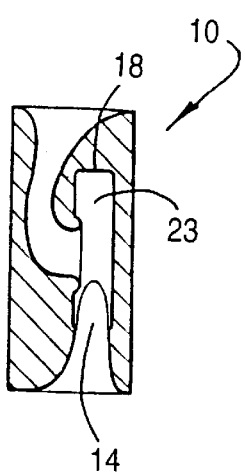
FIG. 3d          FIG. 3e          FIG. 3f

NASAL AND ORAL FILTERS

This is a continuation of application Ser. No. 08/793,487, filed Feb. 26, 1997, now U.S. Pat. No. 5,787,884, which was a national stage of PCT/AU95/00540 filed Aug. 25, 1995.

FIELD OF THE INVENTION

The present invention relates to nasal and oral filters and more particularly to nasal filters adapted to recover fine particulate material from air inhaled or exhaled by a human or other mammalian animal.

BACKGROUND ART

Many people, and other mammalian animals, suffer from asthma, rhinitis and other diseases caused by the inhalation of aeroallergens. In order to understand the nature of the disease and possible treatments it would be desirable to be able to collect these aeroallergens from the inhaled air stream. Such collections could also act as a prophylactic measure.

While there is strong epidemiological evidence associating exposure to aeroallergens to both sensitisation and symptoms at a communal level, and to a lesser extent at an individual level, the methods for estimating personal exposure to aeroallergens are poorly developed. The most common method is to measure allergen concentration in settled dust (collected by a vacuum cleaner) which functions as a source of aeroallergens. The method has, however, serious confounders such as the concentration of allergen and quantity of dust/area varying more than 10 fold at different sites within a room. There is, however no data to directly show that such samples relate to individual personal exposure. Others have attempted to measure aeroallergens on stationary filters using an air pump. With this method the amount of aeroallergen per time or volume differs markedly with degrees of dust disturbance and pump flow rates. Generally, measurement of settled and airborne dust correlate only weakly with one another, if at all. Outdoor allergen sources, such as fungal spores or fallen particles, are estimated and generalised with spoor traps.

The best available method generally used to measure personal exposure is to use filters worn on the upper body. These were developed for occupational sampling eg. for asbestos and coal. Although they have been used occasionally for allergens they cannot be widely applied. This application is limited by battery life, low flow rates, consequent small samples and the relatively high cost of such sampling devices. Such filters may not reflect what is actually being inhaled for several reasons. Firstly, spatial distribution of allergenic particles differs over small distances. For instance, in bed the face is close to the allergen source and the allergen may not travel to a filter a half metre away. Secondly, the collection of particles onto a vertical filter surface with a low constant face velocity is significantly different from such a collection involving variable airflow into a person's nostrils. Variables include changes in flow between and within each cycle of respiration and with exercise, and the effects of thermal body drafts, movement and wind.

Airborne allergens are mainly carried by large particles, although this varies with both the allergen involved and the circumstances. Mite allergens are mainly carried by mite faeces (>90% allergen 10–40 $\mu$ particles); cat allergens with dander particles (~70% associated with >~3 $\mu$ particles); fungal allergens depend upon the species and maturity (3 to 90 $\mu$); pollen depending upon the species (15 to 60 $\mu$, mainly 20 to 30 $\mu$). What is airborne is dynamic and changes with time; small particles, for instance, have lower settling speeds and remain airborne for longer.

The nose of humans and other mammalian species efficiently collects particles, such as dust, pollen, and bacteria, onto the mucosa by a combination of turbulence and impaction. Efficiency is determined by particle velocity, angular velocity, mass, size and shape of the particle and the route that the particle takes in the nose.

There have been reports (Pasricha J. S. & Abrol B. M. Ann. Allergy 1974; 32: 331–333; French Patent specifications 2,536,659, and 2,504,003; U.S. Pat. Nos. 4,401,117 and 5,117,820) of the insertion of a tube containing a filter such as a wire mesh sieve into the nose for the purpose of relief of inhalant allergy. The use of such a wire filter with a:pore size capable of removing most particles associated with allergy (ie. those >5 $\mu$ diameter) could be expected to have high airflow resistance and to be uncomfortable to use. In addition, as such a filter becomes loaded with particles its resistance would increase making it more difficult to use. In addition particulate material collected by such filters would be more difficult to completely remove in an unadulterated (virgin) state and so would not be in a form suitable for direct analysis.

DISCLOSURE OF THE INVENTION

In its broadest aspect the invention consists in particle entrapment means for the capture of particles in an inhaled or exhaled air stream, the particle entrapment means comprising a body having a portion adapted to fit within the mouth or at least one nostril of a human, or other mammalian animal, in sealing engagement with the edges of that orifice, and a passage through the body to allow air to be inhaled or exhaled by the animal through the particle entrapment means, the passage having a non-linear path, being of a minimum cross sectional area very much larger than the maximum cross sectional area of the particulate matter likely to be entrapped and including collection means so placed in the passage that, in use, particulate matter in air inhaled by or exhaled by, the animal will be caused to impact against the collection means due to the non-linearity of the passage and to be retained on the collection means.

The principle use of the devices according to this invention is the capture of potentially allergenic particles in inhaled air. The devices may also be used to collect particles in exhaled air. The exhaled air may contain shed viruses or mycobacteria indicative of particular respiratory disease states. Such collected particles could be subject to diagnostic procedures such as by culture, by antibody probing or by nucleic acid analysis.

The non-linear passage through the particle entrapment means is adapted to allow substantially free inhalation and/or exhalation at least when a wearer is at rest. For this reason the passage is very much larger in cross sectional area than the maximum cross sectional area of the particles likely to be entrapped. Preferably the cross sectional area of the passage will be many orders of magnitude greater than the cross-sectional area of the individual particles of interest. Typically such particles have cross-sectional areas of from 3 to 2000 sq $\mu$m (i.e. the particles have diameters from 1 to 50 $\mu$m). Typically the cross-sectional area of the passage is at least 5 sq mm, preferably 10 sq mm. The nasal filter may be provided with a small number of passages, preferably no more than 5, rather than a single passage. In this case it is preferred that the total cross-sectional area of the passages amounts to at least 7 sq mm and more preferably at least 10 sq mm.

The particle entrapment means will preferably be such that the inlet to the passage will, in use, be positioned closely adjacent to the orifice into which the means is fitted. In this way it is ensured that the air passing through the passage is representative of the air that the user would have inhaled were the means not in use. The trapped particles are thus representative of particles that are inhaled by the user.

In one form of the invention the entrapment means may be a cigarette-like device adapted to fit into a users mouth. The lips may seal around an end of the body so that inhaled air is drawn through the passageway.

In another form of the invention the particle entrapment means is inserted into a nostril of a user. In this aspect the invention consists in a nasal filter comprising a body adapted to fit within a nostril of a human, or other mammalian animal, means to cause an outer surface of the body to resiliently engage an adjacent surface of a nostril into which the nasal filter is positioned so as to retain the nasal filter in the nostril, and a passage through the body to allow air to be inhaled by the animal through the nasal filter, the passage having a non-linear path and including collection means so placed in the passage that, in use, particulate matter in air inhaled by the animal will be caused to impact against the collection means due to the non-linearity of the passage and to be retained on the collection means.

In another aspect the present invention consists in a method for the capture of particulate matter passing through the mouth or a nostril of a human or other mammalian animal comprising inserting into the mouth or a nostril of the animal a particle entrapment means according to this invention and causing the animal to inhale through said mouth or nostril.

As the preferred form of the invention is the nasal filter form the following specification will generally concentrate on this form of the invention. It is to be understood that the invention is generally applicable to particle entrapment means for insertion into either the mouth or nostrils.

The method and filter according to the present invention may be used to collect particles of various origins, including biological, organic or mineral, for sampling. Some examples would include pollens, microbiological material, dander, debris, dust of all sorts, asbestos fibres and spores which can later be removed from the nasal filter for analysis. They may also be used to collect particles to prevent exposure to the particles through inhalation. The filters can thus have a therapeutic, protective or prophylactic function. As one example the nasal filter and method according to this invention could be used to reduce exposure to allergens and thus reduce symptoms of hay fever.

While the invention will have most applicability to humans it may also be used in the diagnosis and/or treatment of similar aeroallergen diseases in other mammalian animals. It may have particular applicability in racing horses or dogs, in prize livestock and in household pets.

The body of the nasal filter may be formed of resilient material such as a soft plastics material, a natural or synthetic rubber or a silicone material. Alternatively it may be made of a rigid material such as a rigid synthetic plastics material or a metal. In the latter case it is provided with a resilient surface coating or layer. Alternatively, it may be provided with a resilient foam or inflatable cuff. The use of such a cuff has the advantage that a single filter may be adapted for use in persons with a wider range of nostril sizes than would otherwise be possible. In each case the body of the nasal filter is provided with means to allow it to resiliently engage with the internal surface of a nostril into which it is inserted. It is desirable, though not essential, that the body of the nasal filter forms an hermetic seal with the internal surface of the nostril. The length is preferably short enough to fit fully within a nostril. There may, however, be occasions in which it is desirable, or necessary, to make a nasal filter of such a length that it will protrude from a user's nostril. The filters are preferably clear or flesh coloured to be unobtrusive to a wearer's appearance.

The passage through the body may have any one or many different configurations. The passage should be non-linear to such an extent that it will induce, in inhaled air, movement which will cause deposition of at least some of the particles in the inhaled air on the collection means. The particles may be caused to impact on the collection means due to their inertia causing then to continue in a straight line and impact on the collection means as the air changes direction. Alternatively the particles may impact on the collection means due to centrifugal forces generated by the swirling of the air stream.

Inhaled air will be drawn into the wearer through the passage in the nasal filter. The wearer may also exhale through that passage. Alternatively, the wearer may exhale through a second outflow passage in the nasal filter or through the mouth. Similarly if inhalation through a particle entrapment means positioned in the mouth exhalation may be through the nose, through the inhalation passage in the entrapment means or through a separate exhalation passage therein.

The collection means may comprise a small designated area inside the passage or may comprise all of its surface area. In one preferred embodiment of the invention the passage is bifurcated in a downstream direction. In this embodiment the collection means comprises a surface in axial alignment with the common part of the passage, the collection means being located between the two divergent arms of the passage at the point of bifurcation.

In preferred embodiments of the invention the surface of collection means may be ribbed or otherwise fashioned in a shape to enhance particle collection. Alternatively the surface may be coated with an adhesive or another substance that will enhance particle collection. If desired the collection means may comprise a strip, patch or other piece of material that may be readily removed from the nasal filter. In another preferred embodiment the collection means may comprise a disc of a gel, or a well containing a liquid, that may be transferred directly to an immunoassay for allergens. The collection means may also be treated to neutralise or in some other way react with the particles impacting thereon.

If desired more than one collection means may be provided in the nasal filter. The filter may include a surface to collect particles having a first set of characteristics and another surface to collect particles with another set of characteristics. Thus one may capture very small particles of, say, less then 3 $\mu$ diameter in one part of the filter and another may capture larger particles in another part of the filter.

In the case that the nasal filter is to be used to collect particles for analysis it may be desirable that the nasal filter may be taken apart to facilitate recovery of collected particles from the collection means. It may also be of advantage to form the nasal filter in a number of parts to allow adjustment of the nature of the passage. Such a change may enable the collection of particles only of some preferred size or density. For example one may desire to only collect particles greater than 10 $\mu$ or less than 3 $\mu$ in diameter. There may also be advantage in changing the shape of the passage to adjust for the likely air flow velocity. In one configuration the passage may be adapted to best collect particles under high flow rates and in another configuration it may best collect particles at low flow rates. The passage and/or the collection means may be so constructed that it, or they, change shape with changed flow velocities. Such change may be adapted to maintain substantially constant particle collection characteristics or breathing resistance. The collection means could for example be mounted on a resilient mounting, such as a rubber foam, which will move closer to the inlet at low flow rates and further away at high flow rates.

In another embodiment the passage is adapted to change shape as the air flow changes from inhalation to exhalation. In this way exhalation may be facilitated.

In normal use a nasal filter would be positioned in each of the animal's two nostrils. In order to facilitate insertions and removal of the filters they are preferably joined by a bridge at the distal ends. The bridge may comprise a relatively rigid bridge adapted to hold the two filters in an appropriate relationship to one another. Alternatively they may be handled separately and be joined by an entirely flexible bridge such as a ribbon or thread.

BRIEF DESCRIPTION OF THE DRAWINGS

Hereinafter by way of example only is a preferred embodiment of the invention described with reference to the accompanying drawings in which:

FIG. 1*a* is a partly cut-away, schematic, side elevational view of the face of a person in whose nostrils had been inserted a nasal filter according to the present invention;

FIG. 1*b* is an underneath view of the nasal filters of FIG. 1*a;*

FIG. 1*c* is a partially cut-away, schematic, side elevational view of the face of a person in whose mouth has been inserted a particle entrapment means according to the present invention.

FIG. 2*a* is a vertical sectional view through a nasal filter according to the present invention;

FIG. 2*b* is a schematic perspective view of the nasal filter of FIG. 2*a* showing the passage therethrough as though the body of the nasal filter were transparent; and FIGS. 3*a* to 3*e* shows vertical sectional views through nasal filters according to five different embodiments of the present invention;

FIG. 3*f* is a vertical section through the nasal filter of FIG. 3*c* at 90° to the plane of that figure.

BEST MODE FOR PERFORMING THE INVENTION

The nasal filters 10 according to the present invention are preferably inserted into each nostril 11 in the nose 12 of a user. The two filters 10 are preferably joined at their distal ends by a flexible bridge 13. The bridge 13 facilitates withdrawal of the filters from the nose 12.

As is seen in FIG. 2*a* the nasal filter 10 is formed with an air passage 14 which comprises a y-shaped channel extending longitudinally through a body 15 of the nasal filter 10. The passage 14 includes an inlet 16 of gradually diminishing cross-section in the direction of flow of inhaled air. The inlet 16 terminates at a point of bifurcation of the passage 14 to form a pair of outlets 17. A substantially planar collection area 18 for entrained particulate matter is formed in axial alignment with the inlet 16. The collection area in the depicted embodiment is coated with an adhesive or another substance that will enhance particle collection.

The body is formed of a resilient synthetic plastics material in two parts. The body has a resilient surface coating or layer 24, or may be surrounded by a resilient cuff 25 of a foam material or which is inflatable. An upper part 19 defines a portion of the outlets 17 and the collection area 18. The lower part 21 defines the inlet 16 and a portion of the outlets 17. The parts 19 and 21 are resiliently retained together by interengaging flanges 22.

In use two of the nasal filters 10 are inserted into the nose of a user as is shown in FIGS. 1*a* and 1*b*. As depicted in FIG. 1*c*, the filter 10 can instead be inserted into the mouth 9 of a user, if desired. The user breathes through the nasal filters 10 for a period to collect a sample of inhaled aeroallergens or while he or she is in an environment that may contain potentially deleterious aeroallergens. If a sample of aeroallergens is to be taken the nasal filters 10 can be removed from the nose and separated into its upper and lower portions 19 and 21. The collection area 18 is then exposed and the impacted particulate matter therein recovered for analysis. These particles will have been entrained in inhaled air (as shown by arrows A) and accelerated as they pass through the inlet. As the inhaled air is diverted from its linear path at the bifurcation of the passage 14 at least some of the particles will proceed straight ahead and strike the collection area 18 which is coated with an adhesive or another substance 26 that will cause particles to adhere thereto and enhance particle collection. The air will continue through the nasal filter and emerge from the outlets 17 (as shown by arrows B).

The nasal filters shown in FIGS. 3*a*–3*f* are essentially similar to that described with reference to FIGS. 2*a* and 2*b* and similar parts have been identified by similar numeric indications. The nasal filter shown in FIG. 3(*b*) has two primary collection areas 18 which are adapted to collect particles of differing sizes. The passage 14 of the nasal filter 10 of FIG. 3(*c*) and 3(*f*) includes a swirl or vortex chamber 23. The collection area forms the circumferential wall of the swirl chamber 23. The passage 14 of the nasal filter 10 of FIG. 3(*d*) is helical and substantially any part of the helix could form the collection area 18 under appropriate flow conditions.

The impacted particulate matter may be recovered by scraping the material from the collection area 18 by washing or blowing it therefrom. Thus in those cases, such as the passage 14 in FIGS. 3(*c*), 3(*d*) and 3(*e*), where the collection area 18 is large and/or the passage 14 very convoluted it is still possible to recover samples for analysis. Alternatively, as described above, a strip or patch of removable material 27 may cover the collection means. In this case, the impacted particulate matter is collected for analysis by removing the strip or patch from the filter body.

If the filter body is formed in two portions (FIG. 2*a*) these may be connected together by a screw thread to allow the relative positions of the two portions to be adjusted. In this way it is possible to change the size and/or shape of passage. The size and type of particles impacting on the collection area may be influenced and adjusted.

I claim:

1. Particle entrapment means for the capture of particles in an inhaled, or an exhaled air stream, the particle entrapment means comprising a body having a portion adapted to fit within the mouth or at least one nostril of a human, or other mammalian animal, in sealing engagement with the edges of that orifice, and a passage through the body to allow air to be inhaled by, or to be exhaled by the animal through the particle entrapment means, the passage having a non-linear path and including a collection means so placed in the passage that, during inhalation, air is drawn firstly towards and then secondly around the collection means so that particulate matter in the air inhaled by the animal will be caused to impact against the collection means due to the non-linearity of the passage and to be retained on the collection means such that the particulate matter retained on the collection means is prevented from entering the airways of the animal, said collection means being removable from the particle entrapment means to allow analysis of the particles impacted thereon.

2. A filter comprising a body adapted to fit within a nostril of a human or other mammalian animal, means to cause an outer surface of the body to resiliently engage an adjacent surface of a nostril into which the filter is position so as to retain the filter in the nostril and a passage through the body to allow air to be inhaled by the animal through the filter, the passage having a non-linear path and including a collection means so placed in the passage that, during inhalation air is drawn firstly towards and then secondly around the collection means so that particulate matter in the air inhaled by the animal will be caused to impact against the collection means due to the non-linearity of the passage and to be retained on the collection means such that the particulate matter retained on the collection means is prevented from entering the airways of the animal, said collection means being removable from the filter to allow analysis of the particles impacted thereon.

3. A method for the capture of particulate matter passing through the mouth or a nostril of a human or other mammalian animal comprising:

inserting into the mouth or an nostril of the animal a particle entrapment means for the capture of particles in an inhaled, or an exhaled air stream, the particle entrapment means comprising a body having a portion adapted to fit within the mouth or at least one nostril of a human, or other mammalian animal, in sealing engagement with the edges of that orifice, and a passage through the body to allow air to be inhaled by, or to be exhaled by the animal through the particle entrapment means, the passage having a non-linear path and including a collection means so placed in the passage that, during inhalation, air is drawn firstly towards and then secondly around the collection means so that particulate matter in the air inhaled by the animal will be caused to impact against the collection means due to the non-linearity of the passage and to be retained on the collection means such that the particulate matter retained on the collection means is prevented from entering the airways of the animal, said collection means being removable from the particle entrapment means to allow analysis of the particles impacted thereon; and causing the animal to inhale through said mouth or nostril.

4. A method for the capture of particulate matter passing through the mouth or a nostril of a human or other mammalian animal comprising:

inserting into the mouth or a nostril of the animal a filter comprising a body adapted to fit within a nostril of a human or other mammalian animal, means to cause an outer surface of the body to resiliently engage an adjacent surface of a nostril into which the filter is position so as to retain the filter in the nostril and a passage through the body to allow air to be inhaled by the animal through the filter, the passage having a non-linear path and including a collection means so placed in the passage that, during inhalation air is drawn firstly towards and then secondly around the collection means so that particulate matter in the air inhaled by the animal will be caused to impact against the collection means due to the non-linearity of the passage and to be retained on the collection means such that the particulate matter retained on the collection means is prevented from entering the airways of the animal, said collection means being removable from the filter to allow analysis of the particles impacted thereon; and causing the animal to inhale through said mouth or nostril.

\* \* \* \* \*